United States Patent [19]

Harris

[11] 4,281,190

[45] Jul. 28, 1981

[54] PROCESS FOR PREPARING N-[2-(P-HYDROXYPHENYL)-ETHYL]-P-CHLOROBENZAMIDE

[75] Inventor: Nicholas Harris, Norwich, N.Y.

[73] Assignee: Morton-Norwich Products, Inc., Norwich, N.Y.

[21] Appl. No.: 177,906

[22] Filed: Aug. 14, 1980

[51] Int. Cl.³ .......................................... C07C 103/78
[52] U.S. Cl. .................................................... 564/185
[58] Field of Search ........................................ 564/185

[56] References Cited

U.S. PATENT DOCUMENTS 3,706,796 12/1972 Blake ............................... 564/185 X
3,781,328 12/1973 Witte et al. ............................ 560/42

OTHER PUBLICATIONS

Witte et al., CA 79: 18434k, (1970).
Witte et al., CA 87:134699q and 134700h, (1977).

*Primary Examiner*—Thomas A. Waltz
*Attorney, Agent, or Firm*—Anthony J. Franze

[57] ABSTRACT

A process for preparing N-[2-(p-hydroxyphenyl)ethyl]-p-chlorobenzamide, a penultimate precursor for bezafibrate, is described.

1 Claim, No Drawings

PROCESS FOR PREPARING N-[2-(P-HYDROXYPHENYL)-ETHYL]-P-CHLOROBENZAMIDE

This invention is concerned with the preparation of bezafibrate 2-[p-[2-(p-chlorobenzamido)ethyl]phenoxy]-2-methyl propionic acid). This compound is known to be an effective hypolipemic drug [Unlisted Drugs 29: No. 9,146 (1977)]. It is also described in U.S. Pat. No. 3,781,328.

Heretofore the preparation of N-[2-(p-hydroxyphenyl)ethyl]-p-chlorobenzamide, the penultimate compound in the synthesis of bezafibrate by reaction with ethyl 2-bromo-2-methyl propionate followed by hydrolysis, involves the use of tyramine. Tyramine is a very expensive chemical. Hence, a synthetic route to bezafibrate avoiding the use of tyramine is desirable.

It has been discovered that the penultimate compound in the synthesis of bezafibrate can be produced by an alternative process which does not employ tyramine. Schematically this process is depicted thusly:

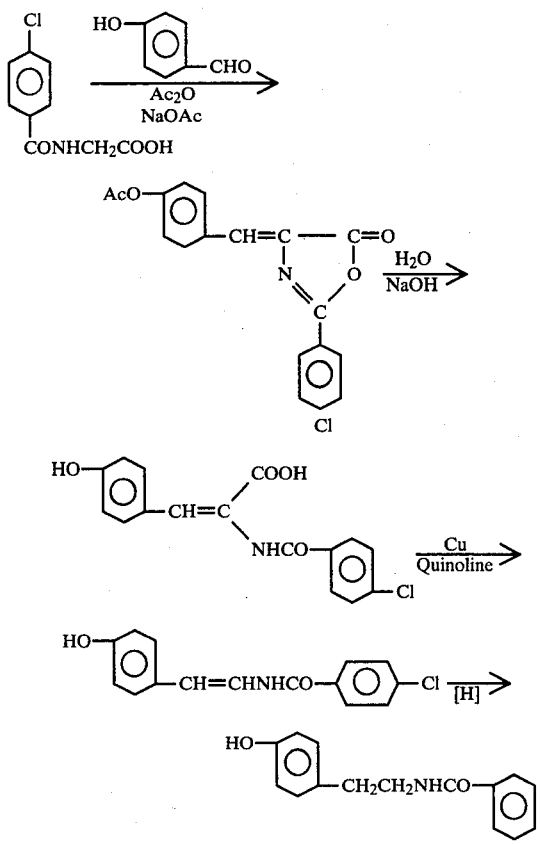

In order that this invention may be fully available to and understood by those skilled in the art the following illustrative example is supplied:

A. 4-(p-Acetoxybenzylidene)-2-(p-chlorophenyl)-5-oxazolone

A mixture of 60 g of N-(p-chlorobenzoyl)glycine, 34.5 g of p-hydroxybenzaldehyde, 23 g of fused sodium acetate and 170 ml of acetic anhydride was heated under reflux for 1 hour. The reaction mixture was cooled slightly and 400 ml of ethanol was added. A solid precipitated on cooling and was filtered and washed with cold ethanol and cold water. An analytical sample was made by recrystallization from $CCL_4/EtOH/AcOH$, m.p. 185–186.

B. 2-(p-chlorobenzamido)-3-(p-hydroxphenyl)acrylic acid

A mixture of 48 g of the substituted 5-oxazolone (A), 290 ml of acetone, 120 ml of water, and 75 ml of 28% aqueous sodium hydroxide solution were heated under reflux for 1 hour. Cooled the reaction mixture, collected the solid product, and washed with water. An analytical sample was made by recrystallization from water/acetic acid, m.p. 239°–240° (dec.).

C. 1-(p-chlorobenzamido)-2-(p-hydroxyphenyl)ethylene

A mixture of 30 g of the substituted acrylic acid (B), 3.2 g of copper powder, 250 ml of quinoline, and 0.1 g of +-butylcatechol was blanketed with nitrogen and heated at 230°–238° C. for 30 min. The cooled reaction mixture was then filtered and the filtrate poured onto an excess of dilute hydrochloric acid. A solid precipitated and was collected and washed with water. An analytical sample was prepared by recrystallization from 80% aqueous ethanol, m.p. 243°–244°.

D. N-[2-p-hydroxyphenyl)ethyl]-p-chlorobenzamide

A mixture of 5 g of 1-(p-chlorobenzamido)-2-(p-hydroxyphenyl) ethylene, 150 ml of a 50/50 mixture of methanol and ethanol, and 0.1 g of platinum oxide was reduced on a Parr shaker at 3 atmospheres and room temperature in 15 minutes. Filtration and evaporation of the filtrate gave 4.5 g of product. An analytical sample was made by recrystallization from dilute aqueous alcohol, m.p. 170°–172°.

What is claimed is:

1. The method of preparing N-[2-(p-hydroxyphenyl)ethyl]-p-chlorobenzamide which consists in: (a) reacting N-(p-chlorobenzoyl)glycine and p-hydroxybenzaldehyde in the presence of sodium acetate and acetic anhydride to form 4-(p-acetoxybenzylidene)-2-(p-chlorophenyl)-5-oxazolone; (b) treating said oxazolone with sodium hydroxide to form 2-(p-chlorobenzamido)-3-(p-hydroxyphenyl)acrylic acid; (c) decarboxylating said acrylic acid to form 1-(p-chlorobenzamido)-2-(p-(hydroxyphenyl)ethylene; and (d) hydrogenating said ethylene.

* * * * *